US012586202B2

(12) United States Patent (10) Patent No.: US 12,586,202 B2
Tiwari et al. (45) Date of Patent: Mar. 24, 2026

(54) SYSTEM AND METHOD FOR AUTOMATIC SEGMENTATION OF TUMOR SUB-COMPARTMENTS IN PEDIATRIC CANCER USING MULTIPARAMETRIC MRI

(71) Applicant: Wisconsin Alumni Research Foundation, Madison, WI (US)

(72) Inventors: Pallavi Tiwari, Madison, WI (US); Rohan Bareja, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 359 days.

(21) Appl. No.: 18/130,693

(22) Filed: Apr. 4, 2023

(65) Prior Publication Data

US 2024/0338828 A1 Oct. 10, 2024

(51) Int. Cl.
*G06T 7/11* (2017.01)
*A61B 5/055* (2006.01)
*G06T 7/149* (2017.01)

(52) U.S. Cl.
CPC ............... *G06T 7/11* (2017.01); *A61B 5/055* (2013.01); *G06T 7/149* (2017.01); *A61B 2503/06* (2013.01); *G06T 2207/10088* (2013.01); *G06T 2207/20081* (2013.01); *G06T 2207/30016* (2013.01); *G06T 2207/30096* (2013.01)

(58) Field of Classification Search
CPC . G06T 7/11; G06T 7/149; G06T 2207/10088;
G06T 2207/20081; G06T 2207/30016;
G06T 2207/30096; A61B 5/055; A61B
2503/06; A61B 5/7267
See application file for complete search history.

(56) References Cited

PUBLICATIONS

Bareja, Rohan ("NIMG-88. A Transfer Learning Approach for Automatic Segmentation of Tumor Sub-Components in Pediatric Medulloblastoma Using Multiparametric MRI: Preliminary Findings") Neuro-Oncology. Nov. 2022. (Year: 2022).*

Zhang, Silu ("A Prior knowledge Based Tumor and Tumoral Sub-region Segmentation Tool for Pedatric Brain Tumors") Arxiv. 2021. (Year: 2021).*

Artzi M, Gershov S, Ben-Sira L, Roth J, Kozyrev D, Shofty B, Gazit T, Halag-Milo T, Constantini S, Ben Bashat D. Automatic segmentation, classification, and follow-up of optic pathway gliomas using deep learning and fuzzy c-means clustering based on MRI. Medical Physics. Nov. 2020;47(11):5693-701.

Bakas S, Akbari H, Sotiras A, Bilello M, Rozycki M, Kirby JS, Freymann JB, Farahani K, Davatzikos C. Advancing the cancer genome atlas glioma MRI collections with expert segmentation labels and radiomic features. Scientific data. Sep. 5, 2017;4(1):1-3.

(Continued)

*Primary Examiner* — Molly Wilburn

(74) *Attorney, Agent, or Firm* — Quarles & Brady LLP

(57) ABSTRACT

The present disclosure provides systems and methods for accurate segmentation of pediatric tumors using MRI images to improve disease diagnosis, prognosis, patient treatment and surgical planning. Specifically, systems and method herein perform segmentation of pediatric tumor sub-compartments using a fully automated transfer learning approach that learns tumor-specific patterns from adult brain tumors and transfers the knowledge to the pediatric brain tumor domain.

20 Claims, 5 Drawing Sheets

(56)                    References Cited

PUBLICATIONS

Bakas S, Reyes M, Jakab A, Bauer S, Rempfler M, Crimi A, Shinohara RT, Berger C, Ha SM, Rozycki M, Prastawa M. Identifying the best machine learning algorithms for brain tumor segmentation, progression assessment, and overall survival prediction in the BRATS challenge. arXiv preprint arXiv:1811.02629. Nov. 5, 2018.

Bareja et al., "A Transfer Learning Approach for Automatic Segmentation of Tumor Sub-compartments in Pediatric Medulloblastoma using Multiparametric MRI: Preliminary Findings" SNO (2022) Poster Presented Nov. 18, 2022.

Barkovich MJ, Li Y, Desikan RS, Barkovich AJ, Xu D. Challenges in pediatric neuroimaging. NeuroImage. 2019;185:793-801. doi:10.1016/j.neuroimage.2018.04.044.

DeNunzio NJ, Yock TI. Modern Radiotherapy for Pediatric Brain Tumors. Cancers. 2020; 12(6):1533. doi: 10.3390/cancers12061533.

Fedorov A, Beichel R, Kalpathy-Cramer J, et al. 3D Slicer as an image computing platform for the Quantitative Imaging Network. Magn Reson Imaging. 2012;30(9):1323-1341. doi:10.1016/j.mri.2012.05.001.

Gillies RJ, Kinahan PE, Hricak H. Radiomics: Images Are More than Pictures, They Are Data. Radiology. 2016;278(2):563-577. doi:10.1148/radiol.2015151169.

Isensee F, Jaeger PF, Kohl SAA, Petersen J, Maier-Hein KH. nnU-Net: a self-configuring method for deep learning-based biomedical image segmentation. Nat Methods. 2021; 18(2):203-211. doi:10.1038/s41592-020-01008-z.

Jaju A, Yeom KW, Ryan Me. MR Imaging of Pediatric Brain Tumors. Diagnostics. 2022;12(4):961. doi:10.3390/diagnostics12040961.

Kawamura A, Nagashima T, Fujita K, Tamaki N. Peritumoral Brain Edema Associated with Pediatric Brain Tumors: Characteristics of Peritumoral Edema in Developing Brain. In: Ito U, Baethmann A, Hossmann KA, et al., eds. Brain Edema IX. Springer Vienna; 1994:381-383. doi:10.1007/978-3-7091-9334-1_103.

Madabhushi A, Udupa JK. Interplay between intensity standardization and inhomogeneity correction in MR image processing. IEEE Transactions on Medical Imaging. May 2, 2005;24(5):561-76.

Madhogarhia R, Fathi Kazerooni A, Arif S, et al. Automated segmentation of pediatric brain tumors based on multi-parametric MRI and deep learning. In: Iftekharuddin KM, Drukker K, Mazurowski MA, Lu H, Muramatsu C, Samala RK, eds. Medical Imaging 2022: Computer-Aided Diagnosis. SPIE; 2022:124. doi:10.1117/12.2611551.

McKean-Cowdin R, Razavi P, Barrington-Trimis J, et al. Trends in childhood brain tumor incidence, 1973-2009. J Neurooncol. 2013;115(2):153-160. doi:10.1007/s11060-013-1212-5.

Menze BH, Jakab A, Bauer S, et al. The Multimodal Brain Tumor Image Segmentation Benchmark (BRATS). IEEE Trans Med Imaging. 2015;34(10):1993-2024. doi:10.1109/TMI.2014.2377694.

Ostrom QT, Patil N, Cioffi G, Waite K, Kruchko C, Barnholtz-Sloan Js. CBTRUS statistical report: primary brain and other central nervous system tumors diagnosed in the United States in 2013-2017. Neuro-oncology. Oct. 2020;22 (Supplement_1):iv1-96.

Peng J, Kim DD, Patel JB, Zeng X, Huang J, Chang K, Xun X, Zhang C, Sollee J, Wu J, Dalal DJ. Deep learning-based automatic tumor burden assessment of pediatric high-grade gliomas, medulloblastomas, and other leptomeningeal seeding tumors. Neuro-oncology. Feb. 2022;24(2):289-99.

Quon JL, Chen LC, Kim L, et al. Deep Learning for Automated Delineation of Pediatric Cerebral Arteries on Pre-operative Brain Magnetic Resonance Imaging. Front Surg. 2020;7:517375. doi:10.3389/fsurg.2020.517375.

Richards JE, Xie W. Brains for all the ages: structural neurodevelopment in infants and children from a life-span perspective. Advances in child development and behavior. Jan. 1, 2015;48:1-52.

Rizwan I Haque I, Neubert J. Deep learning approaches to biomedical image segmentation. Inform Med Unlocked. 2020;18:100297. doi:10.1016/j.imu.2020.100297.

Russo DP, Zorn KM, Clark AM, Zhu H, Ekins S. Comparing multiple machine learning algorithms and metrics for estrogen receptor binding prediction. Molecular pharmaceutics. Aug. 16, 2018;15(10):4361-70.

Shaari H, Kevrić J, Jukić S, et al. Deep Learning-Based Studies on Pediatric Brain Tumors Imaging: Narrative Review of Techniques and Challenges. Brain Sci. 2021;11(6):716. doi:10.3390/brainsci11060716.

Smith SM. Fast robust automated brain extraction. Hum Brain Mapp. 2002; 17(3):143-155. doi:10.1002/hbm.10062.

Stevens SP, Main C, Bailey S, et al. The utility of routine surveillance screening with magnetic resonance imaging (MRI) to detect tumour recurrence in children with low-grade central nervous system (CNS) tumours: a systematic review. J Neurooncol. 2018;139(3):507-522. doi:10.1007/s11060-018-2901-x.

Taha AA, Hanbury A. Metrics for evaluating 3D medical image segmentation: analysis, selection, and tool. BMC medical imaging. Dec. 2015;15(1):1-28.

Taran S, Taran R, Malipatil N, Haridas K. Pediatric Medulloblastoma: An Updated Review. West Indian Med J. Published online Apr. 11, 2016. doi:10.7727/wimj.2015.294.

Wisoff JH, Sanford RA, Heier LA, et al. Primary Neurosurgery for Pediatric Low-Grade Gliomas: A Prospective Multi-Institutional Study From the Children's Oncology Group. Neurosurgery. 2011;68(6):1548-1555. doi:10.1227/NEU.0b013e318214a66e.

Zhang S, Edwards A, Wang S, Patay Z, Bag A, Scoggins Ma. A Prior Knowledge Based Tumor and Tumoral Subregion Segmentation Tool for Pediatric Brain Tumors. Published online 2021. doi:10.48550/ARXIV.2109.14775.

Zhou Z, Sodha V, Pang J, Gotway MB, Liang J. Models Genesis. Published online 2020. doi:10.48550/ARXIV.2004.07882.

* cited by examiner

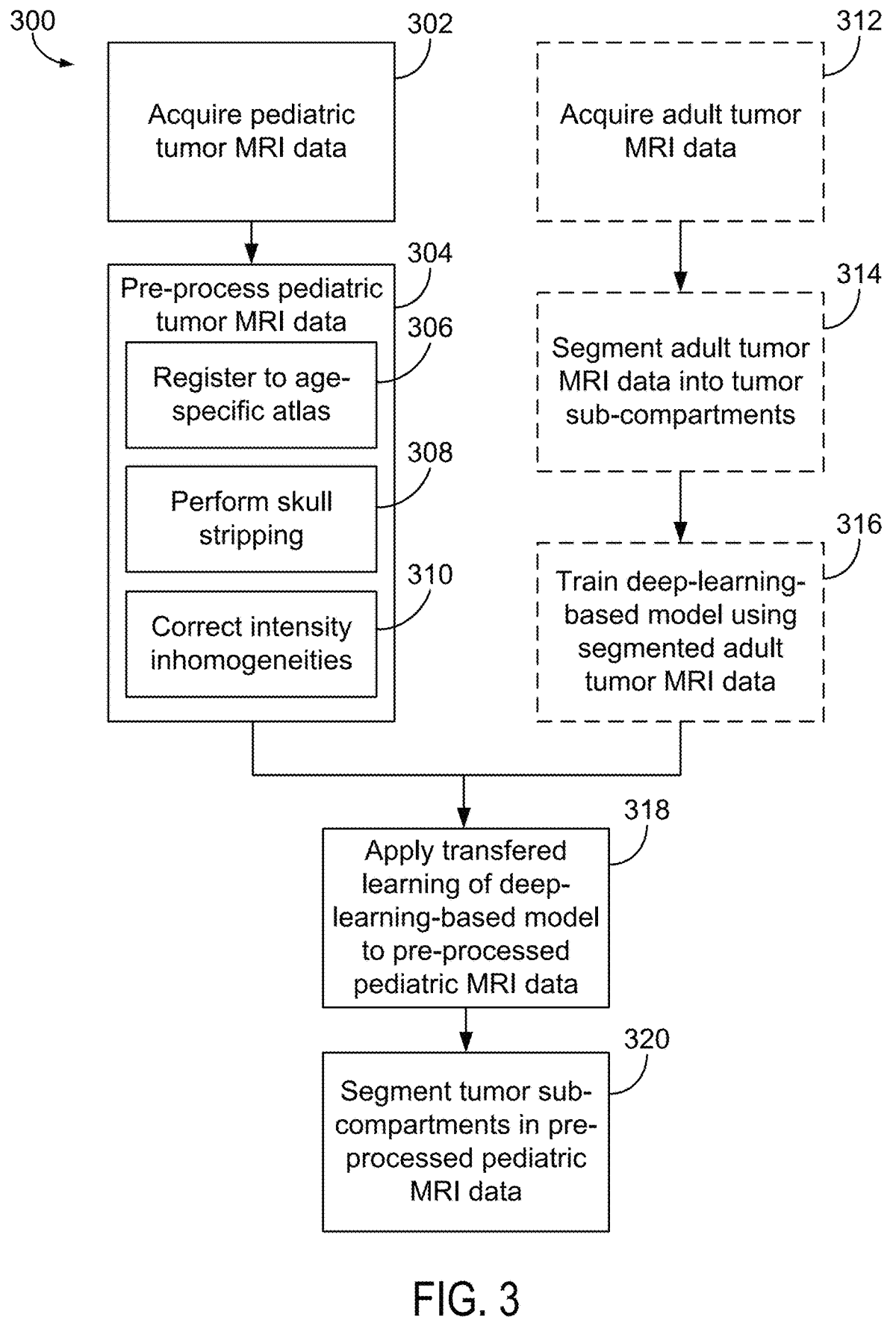

300

302
Acquire pediatric tumor MRI data

304
Pre-process pediatric tumor MRI data

306
Register to age-specific atlas

308
Perform skull stripping

310
Correct intensity inhomogeneities

312
Acquire adult tumor MRI data

314
Segment adult tumor MRI data into tumor sub-compartments

316
Train deep-learning-based model using segmented adult tumor MRI data

318
Apply transfered learning of deep-learning-based model to pre-processed pediatric MRI data 320
Segment tumor sub-compartments in pre-processed pediatric MRI data

FIG. 3

SYSTEM AND METHOD FOR AUTOMATIC SEGMENTATION OF TUMOR SUB-COMPARTMENTS IN PEDIATRIC CANCER USING MULTIPARAMETRIC MRI

CROSS-REFERENCE TO RELATED APPLICATIONS

N/A

STATEMENT OF GOVERNMENT SUPPORT

N/A

BACKGROUND

The present disclosure describes systems and methods for automated MRI image segmentation of brain tumor in pediatric MRI images based on transfer learning deep neural network of adult brain tumor MRI images Medulloblastoma (MB) is the most common malignant brain tumor in children, accounting for 20% of pediatric brain tumors. Current treatment strategies for older children require multimodal therapy inclusive of surgical resection, chemotherapy, and craniospinal irradiation.[2,3] While these tailored therapies have resulted in improving the treatment and survival outcomes in MB, they primarily rely on his-topathological specimens obtained from surgical proce-dures. [4] This requires accurate delineation of the tumor habitat (comprising enhancing tumor, necrotic core/non-enhancing tumor, and peritumoral edema sub-compart-ments).

Currently, there is a lack of automated approaches that could achieve this task in pediatric brain tumors. Manual delineation of the tumor boundaries suffers being time consuming, hard to perform in real-time during surgery, and prone to inter-rater variability.[5,6] Hence a need for auto-mated segmentation models that would allow for accurate segmentation of the MB tumor sub-compartments. This would subsequently aid in developing effective treatment planning strategies[6] and would also decrease the labor on the radiologists to guide the annotation process.

Magnetic resonance imaging (MRI) has played a key role in the non-invasive diagnosis and prognosis of pediatric MB. While providing tumor spatial information, MRI modalities allow for conducting image-feature analysis that can be used to build radiomics and machine-learning-based models for risk-stratification and for predicting treatment response. Accurate identification of the tumor sub-compart-ments is crucial to build these models and achieve effective tailored therapy and improved patient outcomes. In this context, deep learning approaches have emerged as power-ful tools in image modeling, by training networks to under-stand higher to minute image features for classification and semantic segmentation tasks.[8]

Recently, in the context of adult brain tumors, many works have utilized the publicly available data sets, such as the Brain Tumor Segmentation challenge (BraTS)[9,10], to employ convolutional neural networks (CNN)-based archi-tectures for brain tumor segmentation. Unfortunately, most of these available approaches have been developed on adult datasets, perhaps on account of having fewer number of children with brain tumors than adults.[11] Recently, the problem of pediatric brain tumor segmentation has gained attention, where a few deep-learning-based approaches were developed in this context[12], yet with a primary focus on low-and high-grade gliomas.[13-16] While some of these approaches included pediatric MB studies in limited cohort sizes[15,16], they have reported average performance scores for pediatric MB tumor segmentation. Hence, there is a need to build automated segmentation models that primarily focus on pediatric MB tumors.

SUMMARY

The present disclosure addresses the above drawbacks by providing systems and methods for analysis of pediatric MB tumor sub-compartments using a transfer learning approach that learns tumor-specific patterns from adult brain tumors, then transfers the knowledge to the pediatric brain tumor domain. The systems and methods may be fully automated and produce segmented images. Accurate segmentation of pediatric MB tumors on routine MRI scans plays an impor-tant role in disease diagnosis, prognosis, and patient treat-ment, including surgical and radiation planning. Thus, increased accuracy and information yields improved patient outcomes. Furthermore, the systems and methods provided herein are able to increase efficiency and reduce radiologist and clinician time, thereby saving costs, including hours of treatment planning time.

In one aspect of the present disclosure, a computer system for automatic segmentation of tumor sub-compartments in pediatric magnetic resonance imaging (MRI) data is described, the computer system comprising a communica-tions connection configured to receive MRI data of a pedi-atric patient and a parameter from the MRI data to select one of a plurality of age-specific atlases; a processor configured to receive the MRI data and the parameter and configured to carry out steps comprising: pre-processing the MRI data to generate pre-processed MRI data, wherein the pre-process-ing includes registering the MRI data to the age-specific atlas; segmenting the pre-processed MRI data, wherein segmenting includes inputting the pre-processed MRI data into one or more deep-learning-based models trained on adult MRI data to generate segmentation of tumor sub-compartments in the MRI data of the pediatric patient; and a display configured to display the segmentation of tumor sub-compartments in the MRI data of the pediatric patient.

In one aspect of the present disclosure, a method for automatic segmentation of tumor sub-compartments in pedi-atric magnetic resonance imaging (MRI) data is described, the method comprising using a computer processor, access MRI data of a pediatric patient; using the computer proces-sor, receive a parameter from the MRI data to select one of a plurality of age-specific atlases; using the computer pro-cessor, pre-process on the MRI data to generate pre-pro-cessed MRI data, wherein the pre-processing includes reg-istering the MRI data to the age-specific atlas; and using the computer processor, segment the pre-processed MRI data, wherein segmentation includes inputting the pre-processed MRI data into one or more deep-learning-based models and outputting a prediction of an area of one or more tumor sub-compartments in the pre-processed MRI data.

The foregoing and other aspects and advantages of the present disclosure will appear from the following descrip-tion. In the description, reference is made to the accompa-nying drawings that form a part hereof, and in which there is shown by way of illustration a preferred embodiment. This embodiment does not necessarily represent the full scope of the invention, however, reference is thereof made to the claims and herein for interpreting the scope of the invention.

BRIEF DESCRIPTION OF THE DRAWINGS

FIG. 3 is a flowchart of one, non-limiting example of a method of automatic segmentation of the pediatric tumor MRI data, according to aspects of the present disclosure.

DETAILED DESCRIPTION

Figure 1:
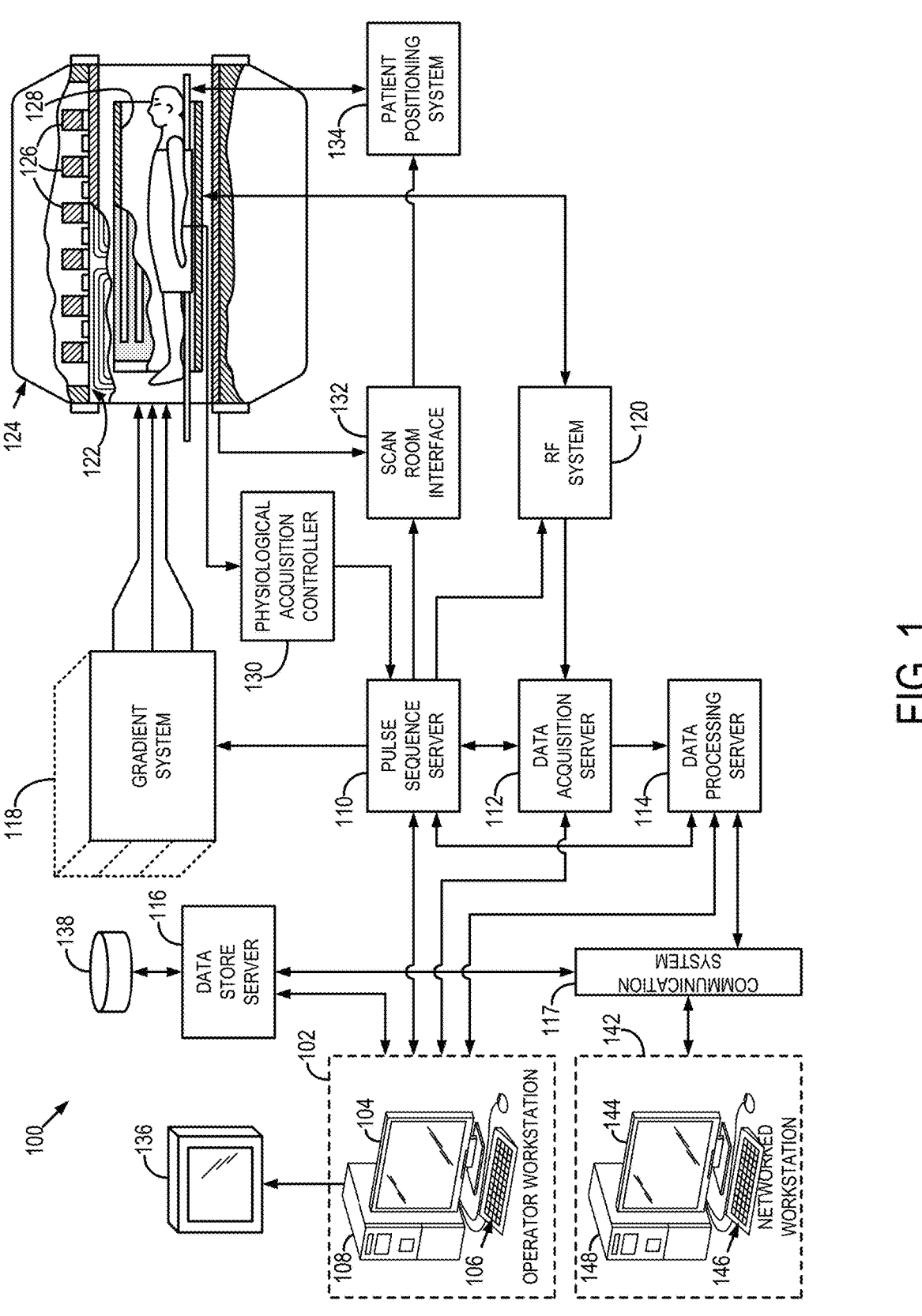
FIG. 1 is a block diagram of an MRI system, according to aspects of the present disclosure.

The present disclosure provides systems and methods for accurate segmentation of pediatric medulloblastoma (MB) tumors on MRI scans to improve disease diagnosis, prognosis, patient treatment, including surgical planning. Specifically, the systems and method provided herein can be used to perform segmentation of pediatric MB tumor sub-compartments using a transfer learning approach that learns tumor-specific patterns from adult brain tumors and transfers the knowledge to the pediatric brain tumor domain. The systems and methods can be fully automated. This transfer learning-based segmentation model can accurately automate delineation of the tumor sub-compartments, yielding more effective surgical and treatment planning in pediatric MB. Hence, the systems and methods provided herein can improve patient outcomes.

In the present disclosure, the systems and methods provided herein can be realized as any of a variety of commercial implementations. For example, in one aspect, the systems and methods may be used to generate computer aided diagnosis (CAD) system or an MRI segmentation tool. Regardless of the particular implementation, the systems and methods provided herein can take pediatric brain MR images and provide tissue segmentation to delineate regions related to tumor evaluation and treatment. These regions may include enhancing tumor, necrotic core/non-enhancing tumor, and peritumoral edema sub-compartments. The systems and methods may provide a trained model that is based on a transfer-learning approach that learned tumor-specific patterns from adult brain tumors, then transferred the knowledge to delineate a pediatric patient-specific brain segmentation for treatment planning. In a non-limiting example, a clinician may be presented with a segmented set of images that present discrete set of tumor related regions, review the automated segmentation, and make final revisions and adjustments for treatment planning.

In one aspect of the present disclosure, a deep learning-based approach is described that segments the tumor habitat, comprising the enhancing tumor (ET), peritumoral edema (ED), and non-enhancing+necrotic core (NET+NEC) sub-compartments, on conventional MRI scans (T1-weighted, T2-weighted, FLAIR). In the model, transfer learning can be utilized, which is defined by transferring the knowledge from a different domain. In a non-limiting example, the approach takes advantage of the image primitives specific to the tumor sub-compartments that are learned from high-grade gliomas in the large dataset of BraTS for adult brains, and then transfers the knowledge over to the target task of segmenting the tumors of our smaller cohort of pediatric MB cases. This new application of transfer learning from adult brain tumors to pediatric brain tumors, contrary to conversion, successfully yielded pediatric MB segmentation.

As used herein, "transfer learning" can refer to the machine learning application of applying the solution developed for one data set to a different but data set. "Deep-learning" can refer to a class of machine learning algorithms that uses multiple layers to progressively extract higher-level features from a raw input. An "atlas" can refer to a brain atlas composed of serial sections along different anatomical planes of the brain. These atlases may include healthy or diseased brains. In a brain atlas, each relevant brain structure is assigned a number of coordinates to define its outline or volume. (age-specific atlas). The "Dice index" represents a performance metric of the transfer-learning-based model. The Dice index, which can also be called the Sørensen-Dice coefficient, is a statistic that can be used to gauge the similarity of two samples. The "Jaccard index" can represent a performance metric of the transfer-learning-based model. The Jaccard index, which can also be called Jaccard similarity coefficient, is a statistic for gauging the similarity and diversity of sample sets. As used herein, "precision" and "recall" can be performance metrics that apply to data retrieved from a set. Precision, which can also be called positive predictive value, is the fraction of relevant instances among the retrieved instances. Recall, also called sensitivity, is the fraction of relevant instances that were retrieved. As used herein, the "Recall index" represents a performance metric of the transfer-learning-based model.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128 in order to perform the prescribed magnetic resonance pulse sequence. Responsive magnetic resonance signals detected by the RF coil 128 are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2},$$

and the phase of the received MR signal may also be determined:

$$\varphi = \tan^{-1}\left(\frac{Q}{I}\right).$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heartbeat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
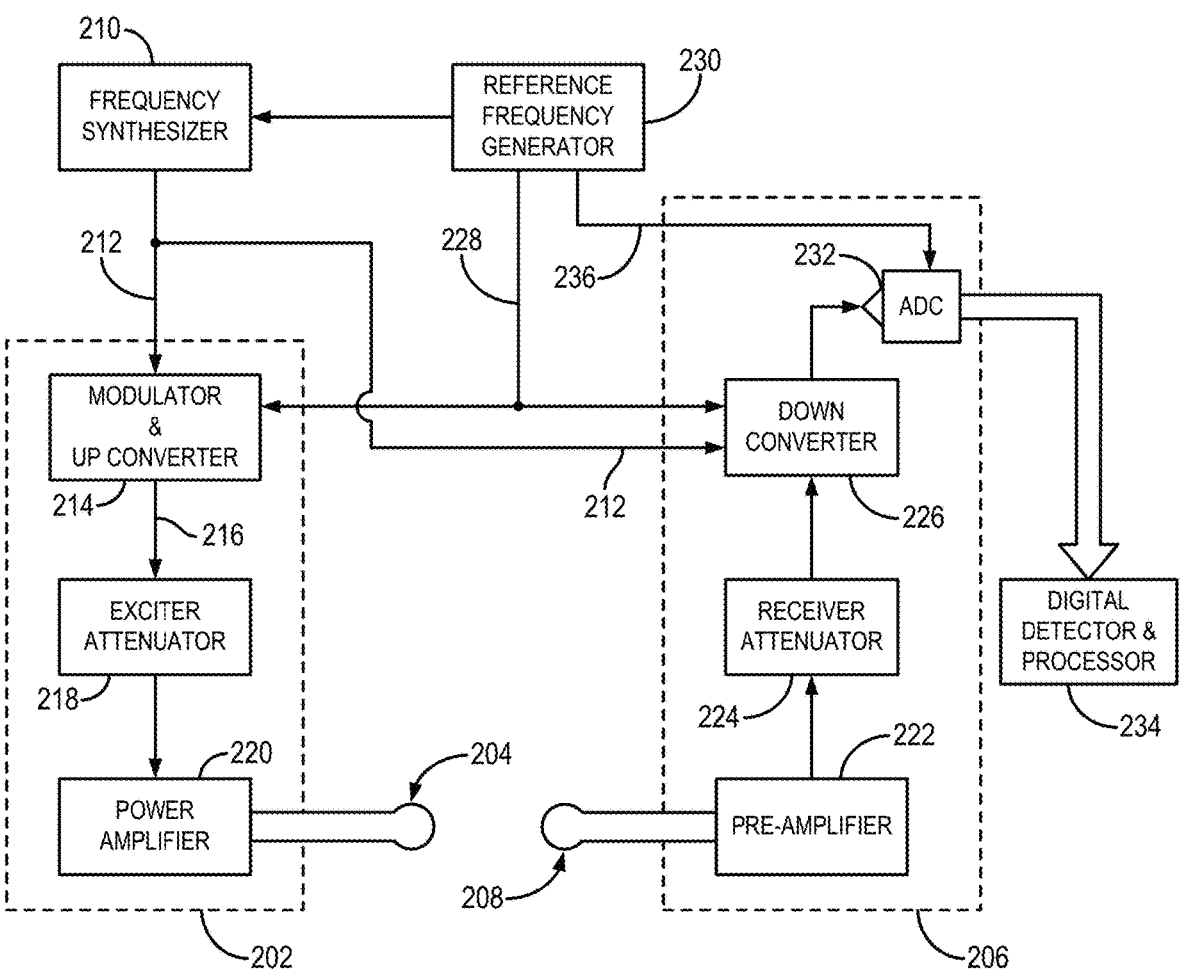
FIG. 2 is a block diagram of an RF system of an MRI system, according to aspects of the present disclosure.

With reference to FIG. 2, the RF system 120 of FIG. 1 will be further described. The RF system 120 includes a transmission channel 202 that produces a prescribed RF excitation field. The base, or carrier, frequency of this RF excitation field is produced under control of a frequency synthesizer 210 that receives a set of digital signals from the pulse sequence server 110. These digital signals indicate the frequency and phase of the RF carrier signal produced at an output 212. The RF carrier is applied to a modulator and up converter 214 where its amplitude is modulated in response to a signal, R (t), also received from the pulse sequence server 110. The signal, R (t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 216 is attenuated by an exciter attenuator circuit 218 that receives a digital command from the pulse sequence server 110. The attenuated RF excitation pulses are then applied to a power amplifier 220 that drives the RF transmission coil 204.

The MR signal produced by the subject is picked up by the RF receiver coil 208 and applied through a preamplifier 222 to the input of a receiver attenuator 224. The receiver attenuator 224 further amplifies the signal by an amount determined by a digital attenuation signal received from the pulse sequence server 110. The received signal is at or around the Larmor frequency, and this high frequency signal is down converted in a two step process by a down converter 226. The down converter 226 first mixes the MR signal with the carrier signal on line 212 and then mixes the resulting difference signal with a reference signal on line 228 that is produced by a reference frequency generator 230. The down converted MR signal is applied to the input of an analog-to-digital ("ND") converter 232 that samples and digitizes the analog signal. The sampled and digitized signal is then applied to a digital detector and signal processor 234 that produces 16-bit in-phase (I) values and 16-bit quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the ND converter 232.

With reference to FIG. 3, an example of a non-limiting workflow 300 is illustrated that can include the step of acquiring pediatric tumor MRI data at step 302. The MRI data may be any convention MRI scan type, such as T1-weighted, T2-weighted, and fluid attenuated inversion recovery (FLAIR). The data may be obtained using an MRI system as that shown in FIG. 1. Alternatively, the data may be previously acquired and accessed from storage, memory, or a network. The MRI data may include any tumor type, such as medulloblastoma or glioblastoma.

At step 304, the pediatric tumor MRI data undergoes pre-processing which may include registering the data to an age-specific atlas (step 306), performing skull stripping to remove the outline of the skull in the data (step 308), and correcting intensity inhomogeneities (step 310). In a non-limiting example all three pre-processing steps 306-308 may be performed. Alternatively, any combination of pre-processing steps 306-308 may be performed.

Registration of the MRI data to an age-specific atlas may be determined by a parameter in the MRI data, such as brain volumetric measurement, cortical thickness estimation, or developmental stage estimation. Alternatively, the age of the subject associated with the pediatric tumor MRI data is determines the appropriate age-specific atlas to utilize in the registration. The age-specific atlas may define individual ages (e.g., 0 years, 1, year, 2 years, etc.) or may define a range of ages (e.g., 0-2 years, 3-5 years, 6-10 years, etc.). In a non-limiting example, the age range for pediatric MRI data spans from 0-18 years.

In a non-limiting example, skull stripping is performed during pre-processing to remove extra-cranial or non-brain tissue is performed to increase the efficiency of segmenting MRI data. Skull stripping may be performed following any one of mathematical morphology-based methods, intensity-based methods, deformable surface-based methods, atlas-based methods, and hybrid methods.

Non-uniformity in the RF coil can cause intensity inhomogeneity distortion, and if not corrected can lead to reduced performance of downstream image processing, and thereby a less effective diagnosis of the imaged structure. In a non-limiting example, the nonparametric nonuniform intensity normalization (N3) algorithm may be applied. In a preferred embodiment, N4ITK bias correction is used.

Other pre-processing functions may also be performed such as brain volumetric measurements, tissue classification, cortical surface reconstruction, cortical thickness estimation, and monitoring the development of the brain.

Steps 312-316 describe the development of a deep-learning-based model for use on the pre-processed pediatric tumor MRI data. These steps are shown as optional, because, in a clinical setting, steps 312-316 have already been performed and, thus, these steps are not repeated. Rather, the result of steps 312-316 (i.e., a trained deep-learning-based model) is utilized to carry out the clinical process. That is, at step 312, adult tumor MRI data is acquired. The MRI data may be any conventional MRI scan type, such as T1-weighted, T2-weighted, and fluid attenuated inversion recovery (FLAIR). The data may be obtained using an MRI system as that shown in FIG. 1. Alternatively, the data may be previously acquired and accessed from storage, memory, database, or network. The MRI data may include any tumor type, such as medulloblastoma or glioblastoma.

In one non-limiting example, a deep-learning-based segmentation approach is applied to the adult tumor MRI data at step 314. At step 316, the deep-learning based segmentation approach is applied to the entire tumor habitat ($I_{TH}$) and tumor sub-compartments. In a non-limiting example, the tumor sub-compartments may include enhancing tumor ($I_{EH}$), peritumoral edema ($I_{ED}$), and the non-enhancing+ necrotic core ($I_{NET+NEC}$) sub-compartments using an nnU-net framework. This results in four pre-trained segmentation models based on each tumor sub-compartment. Thus, the results of steps 312-316 is a trained deep-learning-based model that was trained using adult tumor MRI data.

Returning to the clinical workflow, in a non-limiting example, at step 318, the trained deep-learning-based model is applied, in an implementation of transfer learning, to the prep-processed pediatric tumor MRI data obtained in step 304. Thereafter, the tumor sub-compartments are segmented in the pre-processed pediatric tumor MRI data, at step 320.

Figure 4:
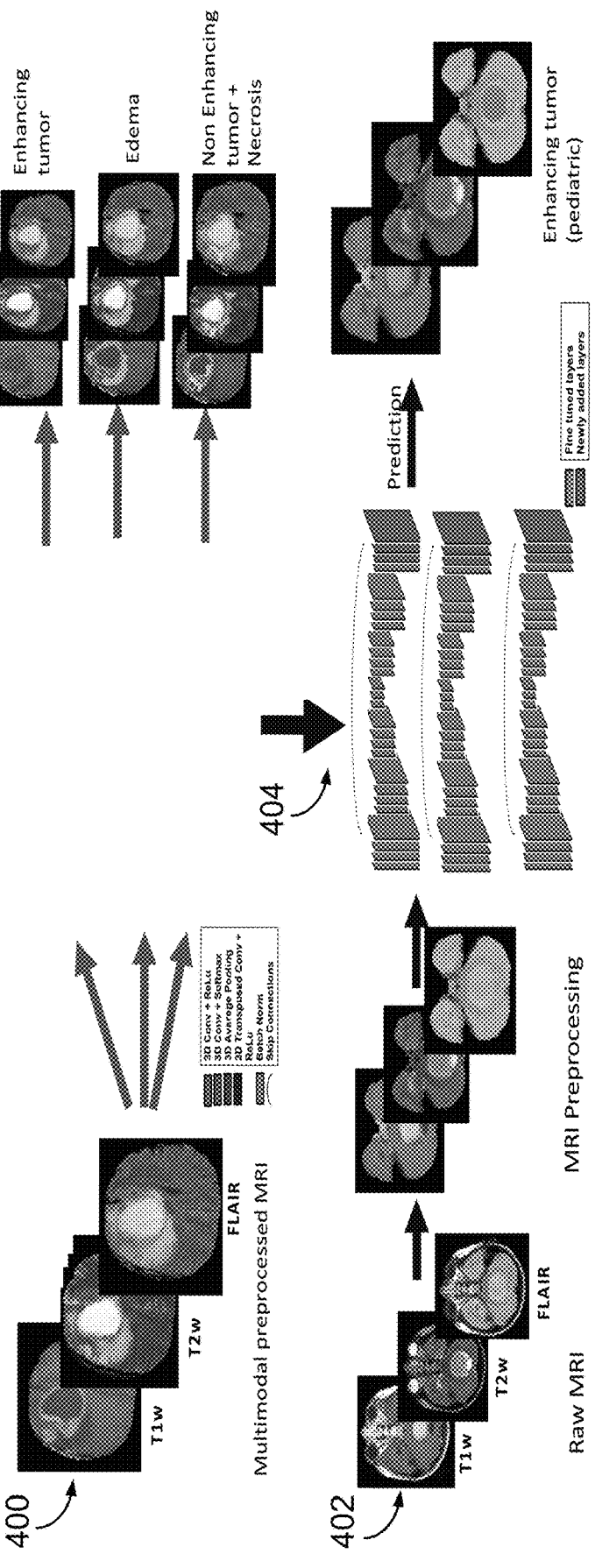
FIG. 4 is a non-limiting example of a workflow of a deep-learning-based model and its transfer to pediatric tumor MRI images to automatically segment tumor sub-compartments, according to aspects of the present disclosure.

Referring to FIG. 4, a non-limiting workflow is illustrated based on the steps of FIG. 3 described above. In a first stage 400, adult brain tumor MIR scans, including T1-weighted, T2-weighted, and FLAIR scans are accessed from the Brain Tumor Segmentation (BraTS) challenge database and used to multiple deep-learning models using an nn-Unet framework. The deep-learning models are specific to predetermined tumor sub-compartments representing enhancing tumor, edema, and non-enhancing tumor and necrosis in adults.

In a second stage 402, the deep-learning models are applied to in a transfer learning approach 404 to adapt models using pediatric tumor MRI scans. Fewer pediatric tumor scans are available than adult tumor scans. The pediatric tumor MRI scans (T1-weighted, T2-weighted, and FLAIR) are pre-processed via registration using age-specific atlases, skull-stripping, and N4ITK bias correction.

An example auto-segmentation of pediatric tumor MRI data according to aspect of the present disclosure are described below:

EXAMPLE

Materials and Methods

Notation

We define an image scene I as I=(C, f), where I is a spatial grid C of voxels $c \in C$, in a three-dimensional (3D) space, $\mathbb{R}^3$. Each voxel, $c \in C$, is associated with an intensity value f(c). $I_{ET}$, $I_{ED}$, and $I_{NET+NEC}$ correspond to the enhancing tumor, peritumoral edema, and the non-enhancing tumor+ necrotic core sub-compartments within every I, respectively, such that $I_{ET}$, $I_{ED}$, $I_{NET+NEC} \subset I$. $I_{TH}$ is the tumor habitat that comprises all the tumor sub-compartments, representing $I_{ET}+I_{ED}+I_{NET+NEC}$.

Workflow

In the first stage of our model, three MRI protocols (Gd-T1w, T2w, FLAIR) are employed to conduct a deep-learning-based segmentation approach on the BraTS dataset involving adult brain tumors. The model is then applied on the three tumor sub-compartments $I_{ET}$, $I_{ED}$, $I_{NET+NEC}$, separately, as well as on $I_{TH}$ (tumor habitat) using nnU-net framework[18], to get four pretrained segmentation models. In the second stage, preprocessing is conducted on our pediatric MB cohort. This includes registration to age-appropriate atlases, skull stripping, bias correction, and intensity matching. Then, we use the pretrained segmentation models form stage 1 to apply transfer learning on the pre-processed pediatric MB MR scans and segment the tumor sub-compartments of each scan. FIG. 1 shows the pipeline for our proposed segmentation model.

Data Curation

Our cohort consisted of 484 adult brain tumor studies (high-grade and low-grade) from BraTS dataset as well as 49 MB studies that were retrospectively collected and ranged between 2 to 18 years in age. The MRI scans of the MB cases were obtained from 2 different institutions: Children's Hospital of Los Angeles (CHLA) (N=19) and Cincinnati Children's Hospital Medical Center (CCHMC) (N=30). The inclusion criteria used for our dataset were: (a) availability of Gd-T1w, T2w, and FLAIR axial view MRI scans; (b) patients with only MB tumors; and (c) acceptable diagnostic quality of the MRI scans, as identified by the collaborating radiologists. Patients with any of poor-quality MRI protocols were excluded. Table 1 shows the demographics of our participating cohorts.

Annotations

The labeling of the tumor habitat, especially in pediatric MRI scans, is often challenging due to the homogeneity of the intensities, as compared to those of adult scans. In our work, ground truth labels were carefully and rigorously generated by 2 experts for $I_{ET}$, primarily based on Gd-T1w scans, and using T2w and FLAIR scans for boundary separation between the tumor and the normal region. The tumor region was annotated manually in each 2D slice of the MRI scans using 3D Slicer[19] by two experienced radiologists (Expert 1 (A.N) with 8 years of experience and Expert 2 (D.M) with 7 years of radiology experience). $I_{ET}$ was defined as the hyperintense region appearing on Gd-T1w image while $I_{ED}$ was defined to be bright on T2w and FLAIR scans. $I_{NET+NEC}$ was stipulated to be gray/dark on Gd-T1w and FLAIR scans, with the only difference being the necrotic sub-compartment ($I_{NEC}$) to be hyperintense on T2w scans. Finally, $I_{TH}$ was defined as the union of the three tumor sub-compartments $I_{ET}+I_{ED}+I_{NET+NEC}$.

Preprocessing

The first step involved performing registration of our MB scans to atlases. Specifically, age-specific atlases were used to account for anatomical differences across the different age groups due to brain development in pediatric patients, where a total of 4 age-specific atlases (0-2, 2-5, 5-10, 10-18 years) were used.[20] We first registered the Gd-T1w images to the age-specific atlases using 3D Slicer[19], and then registered the corresponding T2w and FLAIR scans to the Gd-T1w atlas-registered scan using 3D Slicer.[19] This was done for the purpose of aligning all MRI protocols (Gd-T1w, T2, FLAIR) in the same reference space. This process was followed by skull stripping using Brain Extraction Tool (BET) in FSL.[21] Finally, correction for intensity inhomogeneities was conducted using N4ITK bias correction in 3D Slicer[19], followed by applying an intensity matching approach.[22]

Segmentation of MB Tumors Using nnU-Net and Transfer Learning

Due to the limited sample size, we employed a transfer-learning-based approach to perform segmentations of our MB cases. Specifically, we used nnU-Net framework[18] for building our deep-learning-based model. Initially, the model was trained on adult brain tumors (BraTS 2018) consisting of 387 patients with three MRI modalities (Gd-T1w, T2, and FLAIR)[17], and was validated on 97 patients, for $I_{ET}$, $I_{ED}$, $I_{NET+NEC}$ as well as $I_{TH}$ of the adult brains. Further, transfer learning was incorporated within the nnU-Net framework, using Models Genesis for code changes.[23] This transfer learning method made every layer trainable to perform fine-tuning on our MB cohort.

Experimental Design

Model Architecture and Training

Our nnU-Net segmentation model[18] was trained on BraTS dataset for adult brains using an initial learning rate of 0.01, Stochastic Gradient Descent as optimizer, and a combination of dice and cross-entropy as the loss function. Transfer learning model with Models Genesis was applied[23] to further fine tune every layer on the MB dataset across fivefold cross validation.

Segmentation of the MB Tumor Habitat and the Tumor Sub-Compartments Using Transfer Learning In this experiment, we developed a transfer learning model on the entire tumor habitat $I_{TH}$, comprising $I_{ET}$, $I_{ED}$, and $I_{NET+NEC}$ of the adult brain tumors. Specifically, we first trained a deep learning model on the adult BraTS dataset. After evaluating this model, we performed transfer learning on the tumor habitat of the pediatric MB cohort, which comprises $I_{ET}$, $I_{ED}$, $I_{NET+NEC}$ sub-compartments of the pediatric MB cases.

Additionally, to segment the individual sub-compartments of the tumor, we used the BraTS dataset with three MRI modalities (Gd-T1w, T2w, FLAIR) to develop a separate model for each of the three tumor sub-compartments, namely, $I_{ET}$, $I_{ED}$, $I_{NET+NEC}$. The performance of each of those models was evaluated using fivefold cross validation. Specifically, all the cases from BraTS dataset (for high-grade and low-grade glioma cases) were used to train three separate deep learning models for the three sub-compartments. Those models were then employed to perform transfer learning using nnU-net, on the target task of interest, i.e., the tumor sub-compartments of the pediatric MB cases.

Additionally, for comparison, we trained the deep learning segmentation model directly on the pediatric MB tumors, to compare its performance against that of the transfer-learning-based model.

Results

Experiment 1: Segmentation of the MB Tumor Habitat and the Tumor Sub-Compartments Using Transfer Learning When training the deep learning model on BraTS dataset of adult brains, we obtained dice scores of 0.9±0.005 for $I_{TH}$. Then, when employing this model in our transfer-learning-based model for pediatric MB cases, we obtained a dice score of 0.88±0.03 across fivefold validation runs, for segmenting $I_{TH}$ of MB cases. When we ran the model on an independent test set, we got mean dice score of 0.80 for segmenting $I_{TH}$.

The three separate deep learning models that were devised for the tumor sub-compartments using the BraTS dataset on adult data resulted in dice scores of 0.78±0.02, 0.81±0.1, and 0.62±0.007 for $I_{ET}$, $I_{ED}$, and $I_{NET+NEC}$, respectively. Additionally, when those models were employed to do transfer learning using nn-Unet on our MB cohort, this yielded mean dice scores of 0.83±0.04 for $I_{ET}$, 0.75±0.05 for $I_{ED}$, and 0.55±0.10 for $I_{NET+NEC}$, across fivefold cross-validation runs. When running these models on the independent test set, we got mean dice scores of 0.67±0.20 for $I_{ET}$, 0.54±0.26 for $I_{ED}$, and 0.28±0.30 for $I_{NET+NEC}$.

Figure 5A:
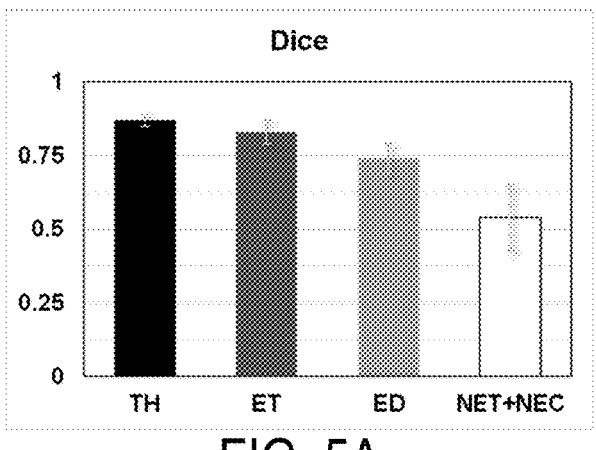
FIG. 5A is a barplot of average dice across 5-fold cross validation, for segmentation of the tumor habitat (TH), enhancing tumor (ET), edema (ED), and non-enhancing+ necrosis (NET+NEC) as performance metrics used to evaluate the performance of the transfer-learning-based segmentation model for the pediatric MB cases, according to aspects of the present disclosure.
Figure 5B:
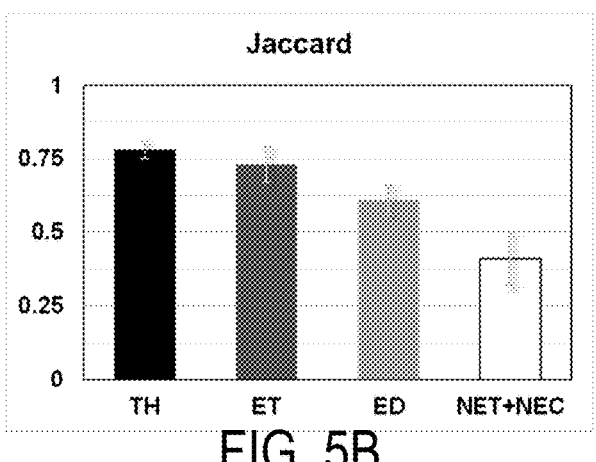
FIG. 5B is a barplot of a jaccard score across 5-fold cross validation, for segmentation of the tumor habitat (TH), enhancing tumor (ET), edema (ED), and non-enhancing+ necrosis (NET+NEC) as performance metrics used to evaluate the performance of the transfer-learning-based segmentation model for the pediatric MB cases, according to aspects of the present disclosure.
Figures 5C, 5D:
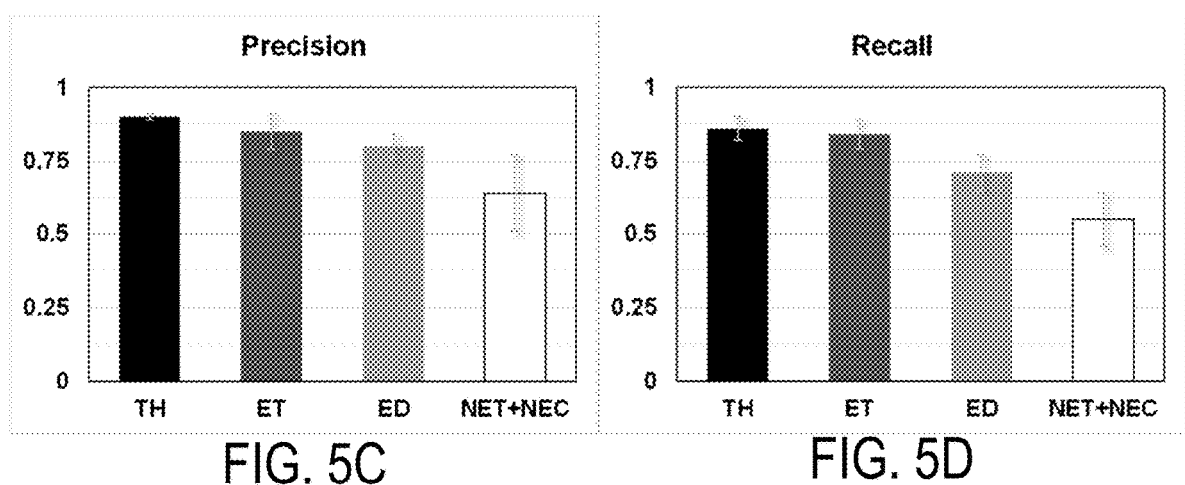
FIG. 5C is a barplot of precision across 5-fold cross validation, for segmentation of the tumor habitat (TH), enhancing tumor (ET), edema (ED), and non-enhancing+ necrosis (NET+NEC) as performance metrics used to evaluate the performance of the transfer-learning-based segmentation model for the pediatric MB cases, according to aspects of the present disclosure.
FIG. 5D is a barplot of recall across 5-fold cross validation, for segmentation of the tumor habitat (TH), enhancing tumor (ET), edema (ED), and non-enhancing+necrosis (NET+NEC) as performance metrics used to evaluate the performance of the transfer-learning-based segmentation model for the pediatric MB cases, according to aspects of the present disclosure.

In Table 2 and FIG. 5, we show the results from the performance metrics we used to assess the performance of our transfer-learning-based segmentation model. Namely, we use the following metrics: Dice coefficient (FIG. 5A), Jaccard Index (FIG. 5B), precision (FIG. 5C) and recall (FIG. 5D) to evaluate the efficacy of our segmentation model.

FIGS. 2, 3, and 4 show samples of our segmentation model results on the pediatric MB cases. In FIG. 2, we show example results where the model was successful in predicting the different tumor labels. Additionally, in FIGS. 3 and 4, we show example results where the model was partially successful in the segmentation task, by either over-segmenting the tumor labels due to their minimal presence in the scans (FIG. 3-a, FIG. 4-b), or under-segmenting them due to different reasons, such as the discrete presence of the label itself (FIG. 3-b, FIG. 4-a), the subtle intensity changes between the different tumor sub-compartments (FIG. 3-c), and the dotted (discontinued) presence of the tumor label on the MRI scans (FIG. 4-c).

Discussion

Accurate segmentation of pediatric brain tumors plays a major role in treatment and surgical planning, yet is still understudied. We present one of the first works that addresses automatic pediatric brain tumor segmentation, and the first to solely focus on pediatric medulloblastoma (MB) segmentation. In our work, we utilized transfer learning along with BraTS (adult brain tumors) dataset, while taking advantage of the image primitives, then transferred the knowledge over for the target task of segmenting pediatric MB tumors. Specifically, segmentations for the entire tumor habitat as well as the tumor sub-compartments including enhancing tumor, edema, non-enhancing+necrosis, were conducted. This transfer learning approach enabled our model to learn features specific to tumors while training on the larger adult dataset, followed by tuning our model specifically for our smaller cohort of pediatric MB cases. Our transfer-learning model yielded mean dice-scores of 0.88±0.03 for the MB tumor habitat, 0.83±0.04 for enhancing tumor, 0.75±0.04 for edema, and 0.56±0.09 for necrotic core+non-enhancing segmentation, across cross-validation runs. On the test set, our model yielded mean dice scores of 0.80±0.10 for the MB tumor habitat, 0.67±0.20 for enhancing tumor, 0.54±0.26 for edema, and 0.28±0.30 for necrotic core+non-enhancing tumor segmentation.

There have been a few studies that explored segmentation of pediatric tumors, primarily gliomas,[13-16] but none were specifically devised for MB. Further, studies have focused on either deep learning or Bayesian approaches,[14,15] but to the best of our knowledge, none has employed transfer learning from adult brain tumors to pediatric tumors successfully. For the previous pediatric brain tumor segmentation approaches that considered MB cases, the reported dice scores from non-enhancing tumor, necrosis, and edema sub-compartments, have been average, underlining the challenges faced in pediatric brain tumor segmentation. Specifically, Peng et al. developed a deep-learning network to automatically segment the tumors of high-grade gliomas, MB, and other leptomeningeal diseases in pediatric patients, on T1 contrast-enhanced and T2/FLAIR images[16]. Similarly, the work in[15] employed a CNN-based model to segment the sub-compartments of multiple pediatric brain tumors, primarily gliomas, and included a limited cohort of MB cases (n=24) in their work. The model processed images at multiple scales simultaneously using a dual pathway. The first pathway kept the images at their normal resolution, while the second pathway down-sampled them. While the model was able to differentiate between the enhancing and non-enhancing tumor compartments of MB tumors, the reported dice scores were relatively low (0.62 for enhancing tumor, 0.18 for edema, and 0.26 for non-enhancing tumor), indicating that the model has under-segmented the tumor sub-compartments. In contrast, our model (0.83, 0.67 for enhancing tumor, 0.75, 0.54 for edema, and 0.56, 0.28 for necrotic core+non-enhancing tumor) consistently yielded high values for most sub-compartments, both on our training and test sets, respectively. Though our model did fairly well in segmenting the MB tumor sub-compartments, we had faced some challenges in our work that we outline below.

We dealt with the problem of class imbalance, as all the three tumor sub-compartments were present in only 70% of the patients. In the remaining 30% of the cohort, some of the sub-compartments were missing. For instance, we found the edema sub-compartment to be rarely present in MB around the tumor core (e.g., in FIG. 3-b), as reported in literature.[26] For the purpose of increasing class representation of edema to improve the model's performance, we labeled edema around the ventricles, since the ventricular edema also has similar features as the peritumoral edema. Additionally, the necrosis sub-compartment has been reported in previous works to be in 40-50% of pediatric MB[27], whereas it was found scarcely in our cohort and had similar visual appearance to the non-enhancing tumor on Gd-T1w and FLAIR scans (FIGS. 3-c, 4-c). For this reason, we combined both these classes, resulting in improved pixel representation, which has been previously employed in BraTS dataset as well[17]. Also, in some instances, distinguishing between enhancing and non-enhancing tumor in our cohort was difficult when the intensity features looked even (FIG. 3-c). We decided to make use of the center of the caudate nucleus region in the Gd-T1w post contrast MRI scans, as an intensity threshold, in determining whether the sub-compartment is enhancing or non-enhancing tumor. If the intensity of region of the tumor core was above the defined threshold, it was labeled as an enhancing tumor region. All regions with intensity values below that threshold were labeled as non-enhancing regions.

Another challenge was the ground truth labeling of the tumor sub-compartments in pediatric tumors, which was found to be difficult as compared to labeling of adult tumors. This is well known in literature, due to many reasons including the rapidly developing brain of children, the average diagnostic quality of MRI scans, and the prominence of MRI motion artifacts as well as anatomic differences.[28] Perhaps on account of these factors, we were also unable to get a perfect registration alignment between Gd-T1w, T2w, and FLAIR modalities. We have also interrogated the patients that gave poor match between the ground truth annotations and our segmentation model results. One of the reasons for poor match was the dotted and the discontinuous labeling of the tumor sub-compartments in some of the patients. However, our transfer-learning-based learning model was able to find those areas where the dotted or discontinued areas were present (FIG. 4-c). Skull stripping was also a major concern in our pediatric MB cohort, where there were some cases with portions of the brain tissue itself being removed during the skull stripping process. This could be due to the subtle intensity differences between the skull and the brain tissues in pediatric brain scans, which makes it challenging to accurately remove the skull from the images using automated approaches. Further, some of the tumors were found to be heterogenous, e.g., mix Conclusions and Future Work This work presented one of the first approaches to segment pediatric medulloblastoma cases. We employed a transfer learning model that learns tumor-specific patterns from adult brain tumors, then transfers the knowledge to the pediatric brain tumor domain. Our results suggest that the proposed automated segmentation model holds promise for improved surgical/radiation treatment via precise tumor delineation and for building robust diagnosis and prognosis tools, for improved patient outcomes. In our future work, we plan to expand on our analysis on a bigger cohort that includes datasets from multiple institutions. This will greatly aid in decreasing the effect of site variability in our model. We also plan to add other types of tumors such as high-grade and low-grade pediatric gliomas.

TABLE 1

Data distribution across training cohorts. Patient demographics (age and survival information) as well as scanner information
Data Distribution

| | CHLA | CCHMC | CHOP |
|---|---|---|---|
| Data | Train | Train | Test |
| Total cases | 18 | 28 | 32 |
| Mean age(years) | 5.4 | 3.85 | 8.8 |
| Mean OS (days) | 2230.67 | 923.28 | 2220 |
| Scan type | T1 FFE axial post-contrast | T1 FFE axial post-contrast | T1 FFE axial post-contrast |
| MR acquisition type | 2D | 2D | 2D |
| Scanning sequence | Gradient recalled (GR) | Gradient recalled (GR) | Spin Echo (SE) |
| Sequence variant | Steady state (SS) | Steady state (SS) | Segmented k-space/Spoiled/ Oversampling phase (SK/SP/OSP) |
| Pixel spacing (mm) | 0.46-1 | 0.46-1 | 2 |
| Slice thickness (mm) | 1-5.8 | 1-5.8 | 2-5 |

TABLE 2

Performance metrics used to evaluate the performance of the proposed transfer-learning-based segmentation model for the pediatric MB cases.

| Metrics | Tumor habitat | | Enhancing | | Edema | | NET + Necrosis | |
|---|---|---|---|---|---|---|---|---|
| | Training | Test | Training | Test | Training | Test | Training | Test |
| Dice | 0.88 ± 0.02 | 0.80 ± 0.10 | 0.83 ± 0.04 | 0.67 ± 0.20 | 0.75 ± 0.05 | 0.54 ± 0.26 | .55 ± .10 | 0.28 ± 0.3 |
| Hausdorff distance | 2.34 ± 0.06 | 2.79 ± 0.51 | 2.4 ± 0.14 | 2.99 ± 0.5 | 2.19 ± 0.12 | 2.49 ± 0.48 | 2.75 ± 0.18 | 3.28 ± 0.93 |
| Fréchet distance | 2.47 ± 0.06 | 2.92 ± 0.52 | 2.55 ± 0.13 | 3.15 ± 0.5 | 2.26 ± 0.12 | 2.55 ± 0.49 | 2.9 ± 0.2 | 3.36 ± 0.92 |
| Jaccard | 0.78 ± 0.03 | 0.69 ± 0.13 | 0.73 ± 0.06 | 0.53 ± 0.21 | 0.61 ± 0.05 | 0.40 ± 0.21 | .41 ± .09 | 0.20 ± 0.24 |
| Precision | 0.90 ± 0.01 | 0.81 ± 0.14 | 0.85 ± 0.06 | 0.82 ± 0.228 | 0.80 ± 0.04 | 0.60 ± 0.31 | .64 ± .13 | 0.31 ± 0.33 |
| Recall | 0.86 ± 0.04 | 0.82 ± 0.12 | 0.84 ± 0.05 | 0.62 ± 0.23 | 0.71 ± 0.06 | 0.63 ± 0.2 | .55 ± .09 | 0.63 ± 0.31 | of enhancing-tumor, non-enhancing, and necrosis, with ill-defined contours that made ground truth labeling to be arduous, and thereby prone to errors.

There were some merits in our approach. First, we have employed data from two institutions, which allowed our model to be generalizable. Another advantage of our study is utilizing the adult BraTS dataset to learn tumor-specific patterns, and then applying transfer learning on the pediatric tumors, instead of training a model directly on pediatric tumors, which is a very difficult task.

The invention claimed is:

1. A computer system for automatic segmentation of tumor sub-compartments in pediatric magnetic resonance imaging (MRI) data, the computer system comprising:

a communications connection configured to receive MRI data of a pediatric patient and a parameter from the MRI data to select one of a plurality of age-specific atlases;

a processor configured to receive the MRI data and the parameter and configured to carry out steps comprising:

pre-processing the MRI data to generate pre-processed MRI data, wherein the pre-processing includes registering the MRI data to the age-specific atlas;

segmenting the pre-processed MRI data, wherein segmenting includes inputting the pre-processed MRI data into one or more deep-learning-based models trained on adult MRI data to generate segmentation of tumor sub-compartments in the MRI data of the pediatric patient; and a display configured to display the segmentation of tumor sub-compartments in the MRI data of the pediatric patient.

2. The computer system of claim 1, where the plurality of age-specific atlases each define a range of ages.

3. The computer system of claim 1, wherein the pre-processing further includes at least one of skull stripping and correcting for intensity inhomogeneity bias.

4. The computer system of claim 1, wherein the tumor sub-compartments are at least one of an enhancing tumor (ET), peritumoral edema (ED), and non-enhancing/necrotic core sub-compartments (NET+NEC).

5. The computer system of claim 1, wherein the MRI data include at least one of T1-weighted MRI data, T2-weighted MRI data, and FLAIR MRI data.

6. The computer system of claim 1, wherein the one or more deep-learning-based models is trained using adult tumor MRI data to identify tumor sub-compartments in adults.

7. The computer system of claim 6, wherein the one or more deep-learning-based models corresponds to each of the tumor sub-compartments.

8. The computer system of claim 7, wherein the tumor sub-compartments include at least one of an entire tumor habitat (TH), enhancing tumor (ET), peritumoral edema (ED), and non-enhancing/necrotic core sub-compartments (NET+NEC).

9. The computer system of claim 6, wherein the adult tumor MRI data include at least one of T1-weighted MRI data, T2-weighted MRI data, and FLAIR MRI data.

10. The computer system of claim 1, wherein the parameter includes at least one of size, age, developmental stage, brain volumetric measurement, cortical thickness estimation.

11. A method for automatic segmentation of tumor sub-compartments in pediatric magnetic resonance imaging (MRI) data, the method comprising:

using a computer processor, access MRI data of a pediatric patient;

using the computer processor, receive a parameter from the MRI data to select one of a plurality of age-specific atlases;

using the computer processor, pre-process on the MRI data to generate pre-processed MRI data, wherein the pre-processing includes registering the MRI data to the age-specific atlas; and using the computer processor, segment the pre-processed MRI data, wherein segmentation includes inputting the pre-processed MRI data into one or more deep-learning-based models and outputting a prediction of an area of one or more tumor sub-compartments in the pre-processed MRI data.

12. The method of claim 11, where the plurality of age-specific atlases each define a range of ages.

13. The method of claim 11, wherein the pre-processing further includes at least one of skull stripping and correcting for intensity inhomogeneity bias.

14. The method of claim 11, wherein the tumor sub-compartments are at least one of an enhancing tumor (ET), peritumoral edema (ED), and non-enhancing/necrotic core sub-compartments (NET+NEC).

15. The method of claim 11, wherein the MRI data include at least one of T1-weighted MRI data, T2-weighted MRI data, and FLAIR MRI data.

16. The method of claim 11, wherein the one or more deep-learning-based models is trained using adult tumor MRI data to identify tumor sub-compartments.

17. The method of claim 16, wherein the one or more deep-learning-based models corresponds to each of the tumor-subcompartments.

18. The method of claim 17, wherein the tumor sub-compartments include at least one of an entire tumor habitat (TH), enhancing tumor (ET), peritumoral edema (ED), and non-enhancing/necrotic core sub-compartments (NET+NEC).

19. The method of claim 16, wherein the adult tumor MRI data include at least one of T1-weighted MRI data, T2-weighted MRI data, and FLAIR MRI data.

20. The method of claim 11, where in the parameter includes at least one of size, age, developmental stage, brain volumetric measurement, cortical thickness estimation.

* * * * *